United States Patent [19]

Polaschegg

[11] Patent Number: 5,098,373
[45] Date of Patent: Mar. 24, 1992

[54] PROCESS FOR CONTROLLING BLOOD PUMPS IN THE EXTRA-CORPOREAL CIRCUIT OF A SINGLE NEEDLE ARRANGEMENT AND APPARATUS THEREOF

[75] Inventor: Hans-Dietrich Polaschegg, Oberursel, Fed. Rep. of Germany

[73] Assignee: Fresenius AG, Fed. Rep. of Germany

[21] Appl. No.: 552,782

[22] Filed: Jul. 16, 1990

[30] Foreign Application Priority Data

Jul. 19, 1989 [DE] Fed. Rep. of Germany ....... 3923836

[51] Int. Cl.⁵ .............................................. A61M 1/03
[52] U.S. Cl. ......................................... 604/5; 604/28
[58] Field of Search ................. 604/4, 5, 6, 22, 28, 604/52, 53, 67

[56] References Cited

U.S. PATENT DOCUMENTS

| | | | |
|---|---|---|---|
| 4,464,164 | 8/1984 | Troutner et al. | 604/5 |
| 4,490,135 | 12/1984 | Troutner | 604/5 |
| 4,596,550 | 6/1986 | Troutner | 604/5 |
| 4,702,829 | 10/1987 | Polaschegg et al. | 604/5 X |
| 4,758,336 | 7/1988 | Bock et al. | 604/5 X |
| 4,940,455 | 7/1990 | Guinn | 604/5 |

*Primary Examiner*—William H. Grieb
*Attorney, Agent, or Firm*—Omri M. Behr

[57] ABSTRACT

The invention is directed to a process and an arrangement for control of blood pumps in an extra-corporeal circuit provided to a single needle arrangement. In order to avoid recirculation, in accordance with the invention it is provided that the arterial and the venous pumps run at an increased throughput rate at the beginning of each pumping phase.

15 Claims, 2 Drawing Sheets

PROCESS FOR CONTROLLING BLOOD PUMPS IN THE EXTRA-CORPOREAL CIRCUIT OF A SINGLE NEEDLE ARRANGEMENT AND APPARATUS THEREOF

FIELD OF THE INVENTION

A process for controlling blood pumps in the extra-corporeal circuit of a single needle arrangement and apparatus therefor.

BACKGROUND OF THE INVENTION

The invention has been developed from a process for the control of blood pumps in an extra-corporeal circuit of a single needle arrangement as is known from the Journal Medizintechnik, Vol. 106, S/86, pages 146 to 148 and is also directed to an apparatus therefor. It is particularly suitable for an extra-corporeal dialysis circuit.

The use of the Single-Needle-Arrangement or other arrangements with a single needle in dialysis has been known for a substantial amount of time. In previous developments, attempts were made to improve the efficiency of the general procedure and to solve the various different problems which arose, such as for example, the improvement of the control of the pumps for carrying out the work cycle. There is basically a common problem with such single needle arrangements which occurs with all known arrangements and which has previously not been addressed because other difficulties and disadvantages appeared to be more important. This problem relates to the recirculation during the procedure of single needle dialysis.

Previously known arrangements utilize either one or two pumps and additionally, one or more clamps, wherein procedures are known wherein the dialyzer is provided with between two pumps or in which it is provided downstream from the venous pump. There are also arrangements in which there are provided additional chambers partially filled with air which can take the form of a surge tank, or expansion chamber, or bags, which can be provided before the arterial pump, between the pumps, or after the venous pump. These known arrangements are activated by controls wherein controls are known whose activation is are time-time dependent, pressure-pressure dependent, pressure-time dependent, volume-volume dependent, or pressure-volume dependent.

In several of the known arrangements, there is utilized a single canula or a monolumenar catheter which is connected to the patient. From this canula or catheter, arterial and venous portions of the tube system are branched off, wherein these branches can be uncoupled from the rest of the system, either by an occluding pump or by a clamp. Furthermore, it is common to all arrangements that a more or less greater part of the already dialyzed blood is again pumped into the extra-corporeal circuit before the dialyzed blood returns to the body. This procedure is known as recirculation. It is discussed in considerable detail in the Journal "Medical and Biological Engineering and Computing", Volume 17, September, 1989, pages 578 to 582.

The recirculation of the blood can have several causes. Reference will be made to the conditions in the fistula. Different streaming conditions will occur depending upon whether the determinative flow resistance to the blood stream is upstream, that is to say, on the arterial side or downstream, that is to say, on the venous side of the fistula. If the resistance is arterial, then during the arterial pumping phase, more blood is removed from the fistula than is delivered arterially. This has the result that a portion of the blood which is pumped into the area upstream of the canula during the venous phase, is sucked back during the arterial phase and is thus recirculated.

With respect to the flow conditions in the canula, it must be noted that at the end of the venous phase, the canula is totally filled with cleaned blood. In the next arterial phase, this is again sucked into the extra-corporeal circuit and thus recirculated. Attempts were made to diminish this problem by providing the canula and the catheter with smaller fill volumes. However, this did not serve to solve the problem of recirculation in a satisfactory manner.

A further aspect of recirculation is due to the hose system utilized. During the venous pump phase, the entire hose system which lies between the venous pump and the arterial pump or clamp is subjected to the venous bath pressure. Because of the flexibility of the hoses and the air buffer present in the arterial pressure probe, the available volume of this part of the extra-corporeal tube system increases and the hose system balloons out. At the end of the venous phase an additional volume of cleaned blood is stored in the tube system between the venous clamp and the arterial pump or clamp, opposite that in a pressure-less condition. In the immediately following arterial phase, this volume is recirculated. Since during this arterial phase an underpressure develops, the available volume is reduced with respect to the pressureless condition. Thus, an additional amount of cleaned blood is pulled out of the venous hose system and thus recirculated. This condition is repeated in each cycle. Suggestions have been made to solve this problem by utilization of additional clamps or specially constructed hose lines. For practical reasons, none of these suggestions have been put into practice since the additional clamps must be provided directly on the patient which considerably interferes with his mobility. The use of special, that is to say, non-expandable hose materials, has considerable disadvantages including not only economic but technical ones.

A further factor which determines the recirculation results from electronic or mechanical delays in the arterial and venous control circuits. Thus, it can occur that the arterial pump is already activated while the venous pump is still in operation or the venous clamp is still open. In the previously known arrangements, no ways have been found to avoid these effects by which the recirculation could, in practical ways, be reduced or prevented.

Recirculation has a decisive influence on the effectiveness of the extra-corporeal circuit and thus upon, for example, the dialysis, as the volume of fluid running through the dialyzer is greater than the actual blood amount which leaves the fistula, by the recirculation portion.

Thus it would be desirable to provide a process and an arrangement of the aforementioned type which substantially avoids the negative effect of recirculation on the effectiveness of the system and thus improves its efficiency and in which the arrangement due to its simpler construction and safer mode of operation is so operated that an amount of blood timewise, independent of the recirculation, can be abstracted from the patient and returned to him.

SUMMARY OF THE INVENTION

The basis of the present invention is provided by arranging to run the arterial and venous pumps at the beginning of their pump cycle at a high throughput rate.

The invention is directed to an arrangement for the control of blood pumps in an extra-corporeal circuit having a single needle arrangement comprising a tri-branched monolumenar canula, having one branch connectible to the patient and of the others, the first is connected to an arterial branch means comprising an arterial pump and an arterial pressure sensor and the second to a venous branch means, comprising a venous pump, a venous pressure sensor and a blood handling apparatus.

The system further comprises a control entity and an arterial and a venous pump regulation arrangement which are connected to said arterial and said venous pressure sensor respectively, as well as to said arterial and said venous pump respectively. The said control entity is further connected with both of said pumps, whereby the signals from said pressure sensors, acting upon said arterial and said venous, pump regulation arrangements respectively act as activation arrangements for each of pumps and respectively.

In a further embodiment, the arrangement further comprises, between the arterial and the venous pumps, a pressure sensor connected to the control entity and for the pressure-dependent control of said pumps.

In a process for the control of blood pumps in an extra-corporeal circuit having a single needle arrangement of the above described type the improvement comprises driving the arterial pump and the venous pump upon activation, at a rate hiher than, suitably at a pumping rate of 1.2 to 3 times the normal throughput rate of the appropriate pumping phase.

Suitably, the pressure uptake means in the flow direction before the arterial pump to exercises pressure control of the arterial pump to obtain the predetermined under-pressure in the shortest possible time after the activation of the pump suitably by driving the arterial pump at its maximum throughput until the achievement of the desired under-pressure and after attainment of the predetermined under-pressure, maintaining the same at a constant level during the entire remaining arterial pumping phase by thereafter driving it with a sufficient throughput to maintain said under-pressure.

Similarly, a pressure uptake means in the flow direction after the venous pump to exercises pressure control of the venous pump to obtain the predetermined back-pressure in the shortest possible time after the activation of the pump suitably by driving the venous pump at its maximum throughput until the achievement of the desired back-pressure and after attainment of the predetermined back-pressure, maintaining the same at a constant level during the entire remaining venous pumping phase by thereafter driving it with a sufficient throughput to maintain said back-pressure.

It is desirable to cause, upon activation, the arterial pump to deliver an under-pressure of $-100$ mmHg to $-200$ mmHg, relative to atmosphere and the venous pump to deliver a back-pressure of $+200$ mmHg to $+300$ mmHg, relative to atmosphere.

The process of the present invention possesses a number of significant advantages. The advantage of the present invention can be more readily understood by a closer consideration of the time relationship of the recirculation. At the end of the venous pump phase there is a positive venous back pressure in the hose system. Thus, taking into account the expandability of the hose system a certain volume of already cleaned blood is forced back into the arterial hose piece. It is thus always located in the segment of the hose system proximal to the canula.

At the beginning of the arterial phase, that is to say, during the conversion of the positive venous back pressure to the negative arterial suction pressure, this blood volume stored in the arterial hose is the first to be moved and only thereafter the blood volume stored in the venous part of the hoses and only last the blood actually in the patient. Thus, there occurs a segmentation of the blood with the already cleaned blood at the tip of the fluid cylinder forwarded by the arterial pump. During this initial phase no blood is transferred from the patient. During the switch from the arterial to the venous phase a similar effect occurs.

The process of the present invention avoids the disadvantages of these effects. In accordance with the invention after activation of the pump, a maximum volume flow is forwarded and accelerated flow of the stored volume occurs, only after removal of this stored volume is the pump switched back to predetermined rate.

In accordance with the invention the pumps can be activated in accordance with a predetermined pump rate/time profile. It is, in fact, possible in accordance with this invention to activate the pumps by means of a pressure control mechanism. For this purpose the arterial pump is so driven that after the activation of this pump the desired arterial under-pressure is achieved as rapidly as possible and this pressure is maintained at a constant level throughout the entire phase.

In accordance with the invention after the switch over at which time the positive venous back pressure is applied, the pressure control ensures that during a time determined by the control switches, the pump is driven at the maximum rate until the predetermined pressure value is obtained only then, is the pump run so that a constant flow is achieved without thereby bringing about damage of the fistula. By means of this mode of proceeding, the blood flow both from and to the patient is maximized. This leads to a substantial increase in the efficiency of the system.

While hereinabove the effect of the invention has been described with reference to the arterial pumps, it will be readily understood by one skilled in the art that venous pump is operated in an analogous manner and would give rise to analogous effects.

With respect to the arrangement, the problem of the invention is solved in that both in the arterial and venous branches pressure sensors are connected with a particular activation mechanism for regulating each pump device which in turn is connected to the control entity and that each regulating device is connected to each appropriate pump. In accordance with the invention the arrangement is provided with an additional regulating mechanism which controls the activation of the pump so that these run at maximum levels at the beginning of their activation and thereafter, their throughput is dropped to provide a constant throughput.

In order to understand the invention it is particularly to be noted that the previously known pressure controls which have been known for the single needle arrangement are limited to the pressure conditions during the throughput step itself and thus, may be additionally provided to the control arrangments of the present invention since these known control arrangements are directed to the switching between the pumping phases whereas, the controls of the present arrangement are directed to the pump rate that is to say, the throughput rate of the pumps.

The invention may be described by reference to the examples in conjunction with the drawings which show:

FIG. 1 is shown in diagrammatic form illustrating the dependence of pump output plotted against activation time of the pump. From this it may be readily seen that upon activation of the pump this runs with a maximum throughput rate and thereafter, the throughput rate sinks to a constant value in order to abstract from and provide to the patient blood at a constant rate.

Figure 1:
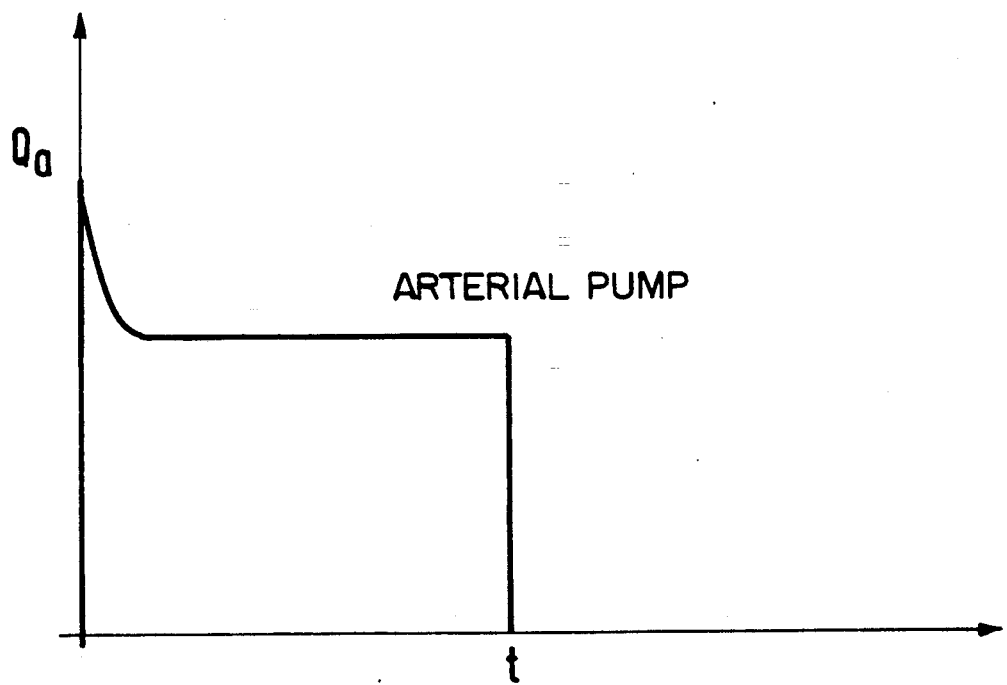
FIG. 1 is a graphic representation of the pump rate/-time profile of the arterial and venous pumps and, FIG. 2 is a schematic representation of the arrangement of the present invention.
Figure 1:
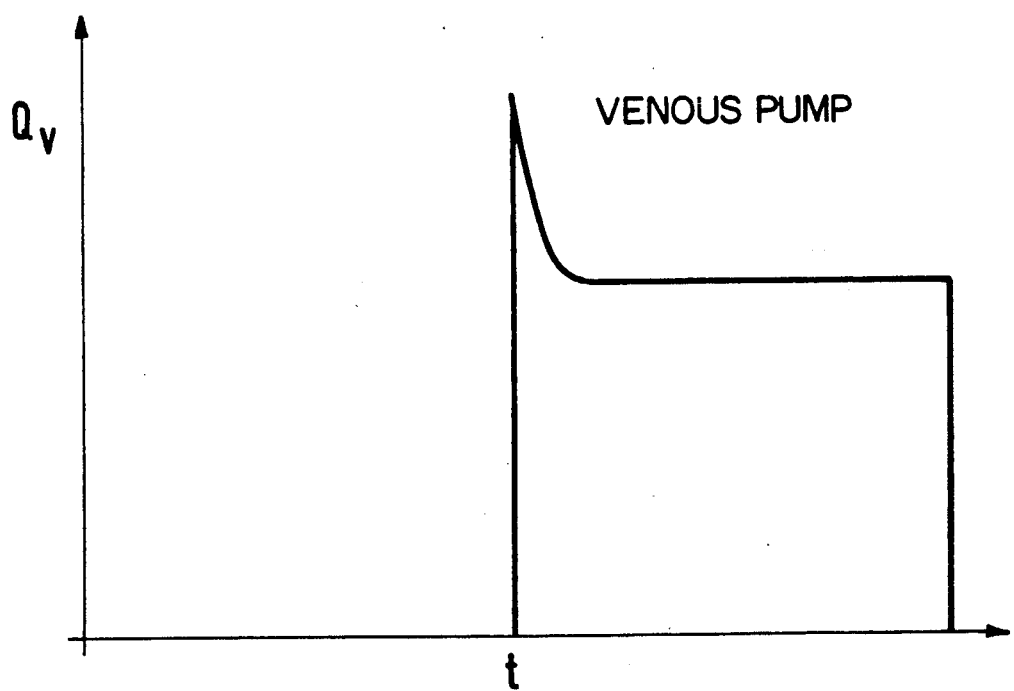
Figure 2:
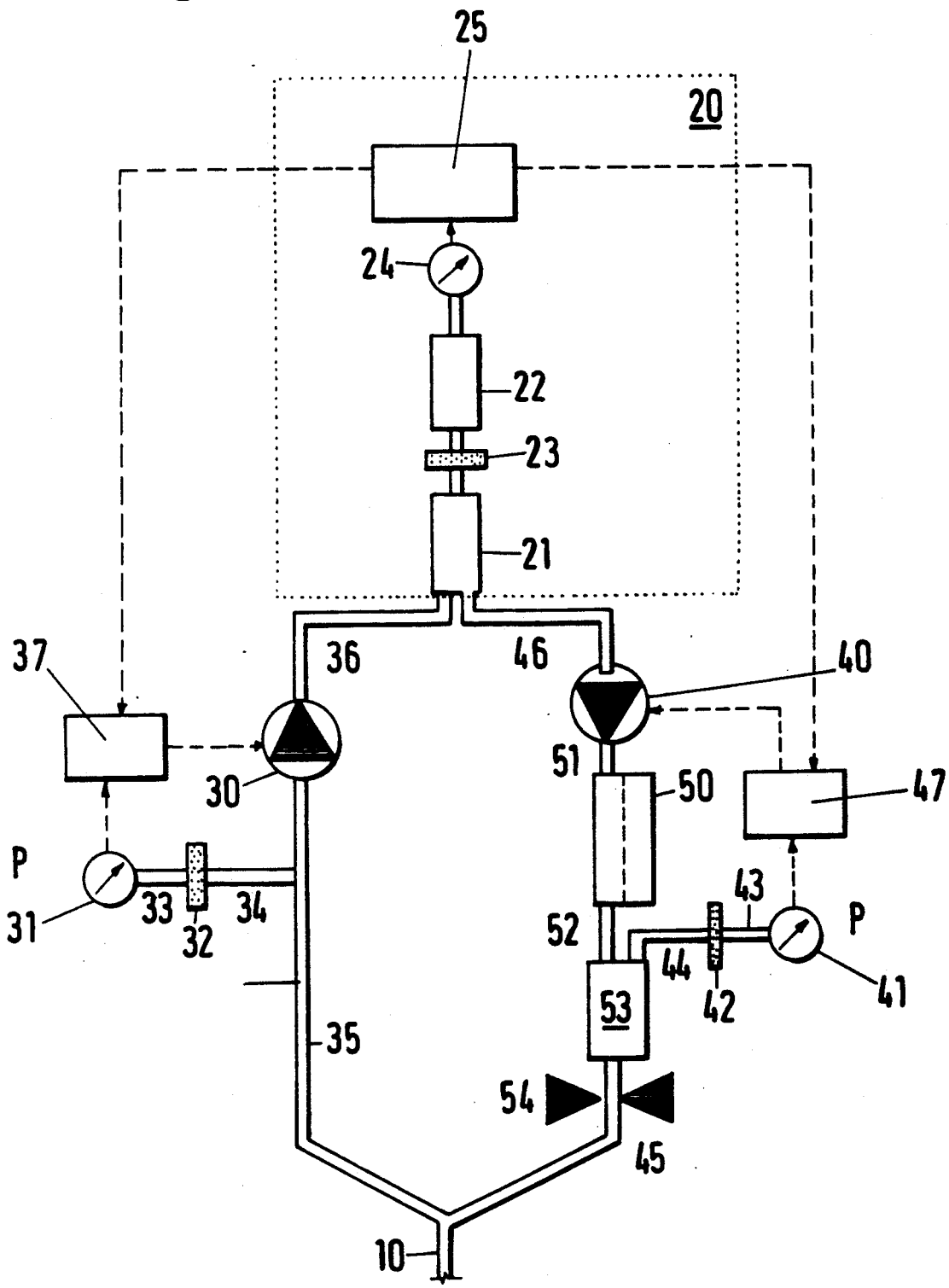
FIG. 2 is a schematic representation of the arrangement of the invention as applied in single needled dialysis.

The arrangement comprises a canula 10 which has a single lumen and which is connected to the patient. The canula 10 branches into an arterial branch 35 and a venous branch 45. In the arterial branch 35 there is provided a arterial pump 30 which is connected, downstream of pump 30 with an expansion chamber 21 by means of hose segment 36. Hose segment 46 runs out of the expansion chamber 21 to venous pump 40 which, in turn, is connected with the venous branch 45. Downstream of venous pump 40 there is provided a hose segment 41 which is connected to dialyzer 50. From dialyzer 50 the treated blood runs via hose segment 52 to a bubble elimination chamber 53, downstream of which is provided venous clamp 54 in branch 45.

In the usual manner expansion chamber 21 is provided with a hydrophobic filter 23 which is connected to a further expansion chamber 22 whose exit end is equipped with pressure sensor 24. The signals from said pressure sensor 24 serve as a pressure/pressure control means by means of a control entity 25.

Control entity 25 is operatively connected with a regulating arrangement 37 and a further regulating arrangement 47 which serve to activate the pumps 30 and 40 respectively.

A pressure sensor 31 and 41 is provided in both the arterial branch as well as the venous branch which, serve to measure the suction pressure of the arterial pump 30 in the arterial branch 35 as well as, the forwarding pressure of the venous pump 40 in branch 45. The pressure sensor 31 is connected with the arterial branch 35 via hose segments 33 and 34 which have a hydrophobic filter 32 therebetween. In an analogous manner, the pressure sensor 41 is connected to bubble chamber 52 via hose segments 43 and 44 having a hydrophobic filter 42 therebetween.

The output values of pressure sensors 31 and 41 are transmitted to regulating arrangements 37 and 47 respectively.

Dialyzer 50 may be replaced by another blood handling arrangement for example, a plasma filter or an absorption arrangement.

Apart from the control arrangements 37 and 47 and the appropriate activating connections with the elements to be controlled corresponding, for example, to the control entity 25 the remaining portion of the apparatus are conventional in the art and therefore, is not illustrated in detail.

The two control arrangements 37 and 47 ensure that after the activation of both the arterial and venous pumps by control arrangement 25 a predetermined suction pressure, as well as back pressure is provided wherein typically, the values lie (relative to atmosphere) between $-100$ mmHg and $-200$ mmHg for the arterial pump and $+200$ mmHg to $+300$ mmHg for the venous pumps.

The invention is not limited to the illustrated example, many more modifications within the framework of the invention would be apparent to one skilled in the art.

I claim:

1. In a process for the control of blood pumps in an extra-corporeal circuit having a single needle arrangement comprising with a canula connected to the patient and, branching from said canula, an arterial branch and a venous branch, comprising an arterial pump in the arterial branch and a venous pump in the venous branch, the improvement comprising driving the arterial pump and the venous pump, upon activation, at a pumping rate higher than the normal throughput rate of the appropriate pumping phase.

2. In a process in accordance with claim 1 the improvement comprising providing a pressure uptake means in the flow direction before the arterial pump to exercise pressure control of the arterial pump to obtain the predetermined under-pressure in the shortest possible time after the activation of the pump.

3. In a process in accordance with claim 2 the improvement comprising, after attainment of the predetermined under-pressure, maintaining the same at a constant level during the entire remaining arterial pumping phase.

4. In a process in accordance with claim 3 the improvement comprising driving the arterial pump at its maximum throughput until the achievement of the desired under-pressure with and thereafter driving it with a sufficient throughput to maintain said under-pressure.

5. In a process in accordance with claim 1 the improvement comprising providing a pressure uptake means in the flow direction after the venous pump to exercise pressure control of the venous pump to obtain the predetermined back-pressure in the shortest possible time after the activation of the pump.

6. In a process in accordance with claim 5 the improvement comprising after attainment of the predetermined back-pressure, maintaining the same at a constant level during the entire remaining venous pumping phase.

7. In a process in accordance with claim 6 the improvement comprising driving the venous pump at its maximum throughput until the achievement of the desired back-pressure with and thereafter driving it with a sufficient throughput to maintain said back-pressure.

8. In a process in accordance with claim 2 the improvement comprising providing a pressure uptake means in the flow direction after the venous pump to exercise pressure control of the venous pump to obtain the predetermined back-pressure in the shortest possible time after the activation of the pump.

9. In a process in accordance with claim 8 the improvement comprising, after attainment of the predetermined back-pressure, maintaining the same at a constant level during the entire remaining venous pumping phase.

10. In a process in accordance with claim 9 the improvement comprising driving the venous pump at its maximum throughput until the achievement of the desired back-pressure with and thereafter driving it with a sufficient throughput to maintain said back-pressure.

11. In a process in accordance with claim 1 the improvement comprising causing, upon activation, the arterial pump to deliver an under-pressure of $-100$ mmHg to $-200$ mmHg, relative to atmosphere.

12. In a process in accordance with claim 1 the improvement comprising causing, upon activation, the venous pump to deliver a back-pressure of $+200$ mmHg to $+300$ mmHg, relative to atmosphere.

13. In a process in accordance with claim 11 the improvement comprising causing, upon activation, the venous pump to deliver a back-pressure of $+200$ mmHg to $+300$ mmHg, relative to atmosphere.

14. An arrangement for the control of blood pumps in an extra-corporeal circuit having a single needle arrangement comprising:

a monolumenar canula 10 connectable to the patient, and connected firstly to an arterial branch means 35 comprising an arterial pump 30, and arterial pressure sensor 31, and secondly to a venous branch means 45, comprising a venous 40 pump, a venous pressure sensor 33 and a blood handling apparatus 50, further comprising a control entity 25, and an arterial 37 and a venous 47, pump regulation arrangement connected to said arterial 31 and said venous 33 pressure sensor respectively as well as to said arterial 30 and said venous 40 pump respectively, said control entity 25 being further connected with both of said pumps 30, 40, whereby the signals from said pressure sensors 31, 41 acting upon said arterial 37 and said venous 47, pump regulation arrangements respectively cause said pump regulation arrangements to act as activation arrangements for each of pumps 30 and 40 respectively and drive the arterial pump and the venous pump, upon activation, at a pumping rate higher than the normal through-put rate of the appropriate pumping phase.

15. An arrangement in accordance with claim 14, further comprising, between the arterial and the venous pumps, a pressure sensor connected to the control entity and for the pressure-dependent control of said pumps.

* * * * *